United States Patent
Filippova et al.

(10) Patent No.: US 11,929,147 B2
(45) Date of Patent: Mar. 12, 2024

(54) DIRECT VARIANT PHASING IN LONG READS TO DETECT QUASISPECIES

(71) Applicant: Roche Sequencing Solutions, Inc., Pleasanton, CA (US)

(72) Inventors: Darya Filippova, Mountain View, CA (US); Khai Luong, Oakland, CA (US); Garima Kushwaha, San Francisco, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 990 days.

(21) Appl. No.: 16/646,962

(22) PCT Filed: Sep. 12, 2018

(86) PCT No.: PCT/EP2018/074639
§ 371 (c)(1),
(2) Date: Mar. 12, 2020

(87) PCT Pub. No.: WO2019/053076
PCT Pub. Date: Mar. 21, 2019

(65) Prior Publication Data
US 2020/0211675 A1 Jul. 2, 2020

Related U.S. Application Data

(60) Provisional application No. 62/558,696, filed on Sep. 14, 2017.

(51) Int. Cl.
*G16B 30/00* (2019.01)
*G16B 20/20* (2019.01)
*C12Q 1/6883* (2018.01)

(52) U.S. Cl.
CPC ............ *G16B 30/00* (2019.02); *G16B 20/20* (2019.02); *C12Q 1/6883* (2013.01); *C12Q 2600/156* (2013.01)

(58) Field of Classification Search
CPC ................................ G16B 30/00; G16B 20/20
See application file for complete search history.

(56) References Cited

U.S. PATENT DOCUMENTS

2011/0097001 A1*  4/2011  Labbi .................. G06K 9/6219
382/225

OTHER PUBLICATIONS

Nielsen, F. (2016). Hierarchical Clustering. In: Introduction to HPC with MPI for Data Science. Undergraduate Topics in Computer Science. Springer, Cham. (Year: 2016).*
András Szolek, Benjamin Schubert, Christopher Mohr, Marc Sturm, Magdalena Feldhahn, Oliver Kohlbacher, OptiType: precision HLA typing from next-generation sequencing data, Bioinformatics, vol. 30, Issue 23, Dec. 1, 2014, pp. 3310-3316 (Year: 2014).*
Stapleton JA, Kim J, Hamilton JP, Wu M, Irber LC, et al. (2016) Haplotype-Phased Synthetic Long Reads from Short-Read Sequencing. PLOS One 11(1): e0147229 (Year: 2016).*
Anthony Rhoads, Kin Fai Au, PacBio Sequencing and Its Applications, Genomics, Proteomics & Bioinformatics, vol. 13, Issue 5, 2015, pp. 278-289 (Year: 2015).*
Bull, R.A., Eltahla, A.A., Rodrigo, C. et al. A method for near full-length amplification and sequencing for six hepatitis C virus genotypes. BMC Genomics 17, 247 (2016) (Year: 2016).*
Cartolano M, Huettel B, Hartwig B, Reinhardt R, Schneeberger K (2016) cDNA Library Enrichment of Full-Length Transcripts for SMRT Long Read Sequencing. PLOS One 11(6) (Year: 2016).*
International Search Report and Written Opinion in PCT/EP2018/074639 dated Nov. 14, 2018; 10 pages.
Cheng, Y. et al.; "Cumulative viral evoluationay changes in chronic hepatitis B virus infection precedes hepatitis B e antigen seroconversion"; *Gut*; vol. 62, No. 9; Sep. 5, 2013; pp. 1347-1355.
Prosperi, M.C.F. et al.; "QuRe: software for viral quasispecies reconstruction from next-generation sequencing data"; *Bioinformatics*; vol. 28, No. 1; Nov. 15, 2011; pp. 132-133.

* cited by examiner

*Primary Examiner* — John S Brusca
*Assistant Examiner* — Jonathan Edward Hayes
(74) *Attorney, Agent, or Firm* — Kilpatrick Townsend and Stockton LLP

(57) ABSTRACT

Described herein are methods for identifying quasispecies of genomes by clustering sequence reads for samples including the genomes based on the similarities of the sequence reads.

19 Claims, 11 Drawing Sheets

| Locus | 1 | 2 | 3 | 4 | 5 | 6 | 7 | 8 | 9 | 10 | ... | N |
|---|---|---|---|---|---|---|---|---|---|---|---|---|
| Sequence Read | | | | | | | | | | | | |
| 1 | A | G | A | T | C | A | C | A | T | G | ... | C |
| 2 | A | G | C | A | A | G | C | A | C | G | ... | C |
| 3 | G | G | A | T | A | A | T | A | T | T | ... | A |
| 4 | A | A | G | A | C | A | C | T | A | G | ... | C |
| 5 | T | G | A | T | C | C | T | G | T | A | ... | A |
| 6 | A | C | G | G | G | A | G | A | C | G | ... | C |
| 7 | A | G | A | G | C | C | C | A | T | T | ... | C |
| 8 | C | T | G | T | T | A | A | T | G | C | ... | G |
| 9 | A | G | A | G | C | G | C | A | T | G | ... | C |
| 10 | C | G | A | T | C | A | T | G | T | G | ... | T |
| 11 | A | G | C | G | G | A | C | A | G | G | ... | C |
| ... | ... | ... | ... | ... | ... | ... | ... | ... | ... | ... | ... | ... |
| M | A | C | A | T | G | A | C | G | T | C | ... | C |

DIRECT VARIANT PHASING IN LONG READS TO DETECT QUASISPECIES

CROSS REFERENCES TO RELATED APPLICATIONS

The present application is a US National Phase Application Under 371 of PCT/EP2018/074639 filed Sep. 12, 2018, which claims priority to U.S. Provisional Patent Application No. 62/558,696, filed on Sep. 14, 2017, both of which are incorporated herein by reference in their entireties for all purposes.

BACKGROUND

Variant analysis can be used in many applications, such as human somatic oncology or identifying drug resistance in viral and bacterial genomes. Traditional variant analysis methods focus on single nucleotide polymorphisms (SNPs), which would not provide phase information of the variants in the genome (i.e., co-occurring SNPs on a same chromosome molecule). Such phase information may be important in resolving how combinations of variants uniquely situated on a homologous genomic region may affect various functions. For example, the co-occurring SNPs may help to identify a subpopulation or a subset of the samples being analyzed, such as detecting quasispecies in mixed viral samples in order to target major and minor viral populations at the same time.

BRIEF SUMMARY

Disclosed herein are techniques for identifying quasispecies or subpopulations of genomes by clustering sequence reads generated from nucleic acids of organisms in a sample. The clustering can be performed based on the similarities of the sequence reads. For example, one or more samples may include multiple organisms having different, but related genomes (e.g., different subspecies of bacteria) or the organisms may have highly similar genomes different by a set of nucleotide variants (e.g., different quasispecies of a viral population). DNA from the one or more samples may be sequenced to generate relatively long sequence reads (e.g., 1000 or more bases for each sequence read). A variant matrix may be generated for the long sequence reads. Each row (or column) of the variant matrix may represent a single long sequence read, and each column (or row) of the variant matrix may correspond to an observed variant that passes a quality check, such as occurring on a sufficient number of long sequence reads (e.g., at a frequency over a threshold value). A hierarchical clustering technique may be applied to the reads (rows or columns) to cluster the reads into different groups in a hierarchical tree. Subspecies may then be determined from the hierarchy of clusters by cutting the tree in a way so as to minimize intra-cluster differences. The information regarding the subspecies may be used for diagnosis and treatment.

These and other embodiments of the invention are described in detail below. For example, other embodiments are directed to systems, devices, and computer readable media associated with methods described herein. Thus, the present invention also encompasses a computer product comprising a computer readable medium storing a plurality of instructions for controlling a computer system to perform an operation of any of the methods above. Furthermore, the invention encompasses system or instrument comprising such a the computer product of claim 19 one or more processors for executing instructions stored on the computer readable medium. Such a system or instrument comprises all means for performing any of the methods above or is configured to perform any of the above methods either in toto or at least modules of said methods.

BRIEF DESCRIPTION OF THE DRAWINGS

The detailed description is set forth with reference to the accompanying figures.

FIG. 2 illustrates example sequence reads in a matrix.

TERMS

Figure 1:
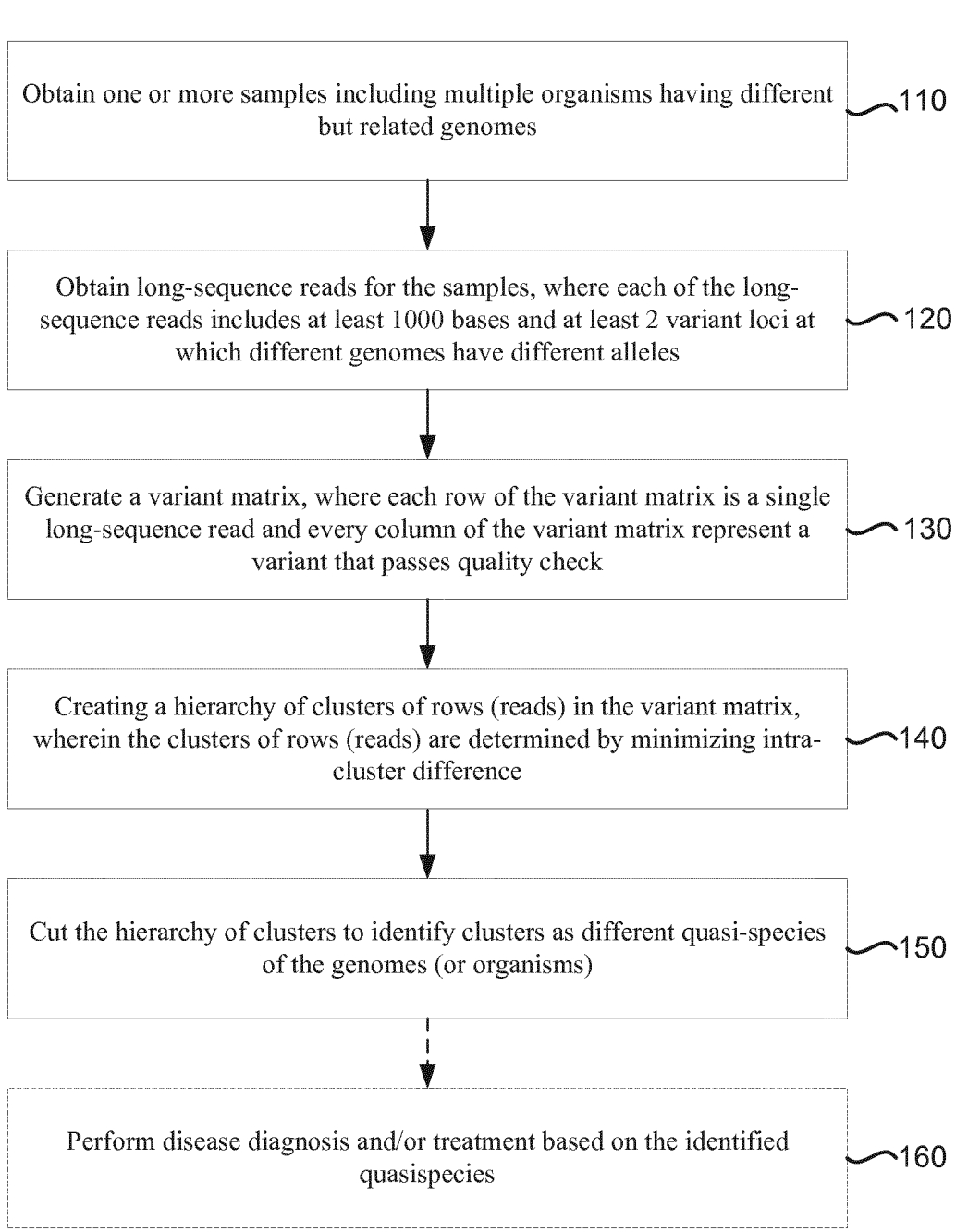
FIG. 1 is a flow chart illustrating an example method of identifying quasispecies based on phased variants in long sequence reads, according to certain aspects of this disclosure.

As used herein, the term "sample" or "biological sample" refers to any composition containing or presumed to contain nucleic acid. The nucleic acid can be from an animal (e.g., mammal, human), plant, microorganism, etc. The term sample includes purified or separated components of cells, tissues, or blood, e.g., DNA, RNA, proteins, cell-free portions, or cell lysates. A sample can also refer to other types of biological samples, e.g., skin, plasma, serum, whole blood and blood components (buffy coat), saliva, urine, tears, seminal fluid, vaginal fluids, aspirate or lavage, tissue biopsies, and other fluids and tissues, including paraffin embedded tissues. A sample can also refer to an environmental sample, such as a water sample. Samples also may include constituents and components of in vitro cultures of cells obtained from an individual, including cell lines. A "test sample" refers to the sample that is under test for detecting variants in the sample.

A variant (also called a variation or mutation) refers to a difference between two sequences. A variant may be, for example, a change of one base to one or more other bases, an insertion of one or more bases, or a deletion of one or more bases. The base or bases at a location in the reference sequence may be referred to as reference allele, while the different base or bases (or insertion or deletion) at the same location on the test sample may be referred to as variant allele. For example, for the single base substitution of A>C, A is the reference allele, and C is the variant allele. The reference allele may be wild type allele representing the most common genotype for the organism occurring in nature. A difference between a sequence read and a target region of a reference sequence can get counted, and a true mutation might be identified (e.g., if enough sequence read show the mutation).

Depth (or coverage) in DNA sequencing is the number of reads that include a given nucleotide in a sequence. Deep sequencing refers to the general concept of aiming for high number of replicate reads of each region of a sequence.

Phasing refers to the task or process of assigning variant alleles (e.g., the As, Cs, Ts and Gs) to a same nucleic acid strand (haplotype), e.g., different strands of different uniploid organisms or the strands corresponding to the paternal and maternal chromosomes of a diploid organism or different strands of different subspecies or quasispecies.

A haplotype refers to a set of nucleotide variations, or polymorphisms, that tend to reside together on a nucleic acid molecule. A haplotype can refer to a combination of alleles or to a set of single nucleotide polymorphisms (SNPs) found on the same nucleic acid molecule, which may be a viral RNA molecule or a chromosome.

A dendrogram refers to a tree-structured graph used to visualize the result of hierarchical clustering. As examples, the result of the clustering may be presented either as the distance or the similarity between the clustered rows or columns depending on the selected distance measure. Various measures can be used to calculate the distance or similarity between rows or columns, including, for example, correlation, cosine correlation, Hamming distance, Tanimoto coefficient, Euclidean distance, city block distance, square Euclidean distance, half square Euclidean distance, etc.

A quasispecies can correspond to a well-defined distribution of mutants that is generated by a mutation-selection process. Selection does not act on a single mutant, but on the quasispecies as a whole. A quasispecies can correspond a cloud of diverse variants that are genetically linked through mutation, interact cooperatively on a functional level, and collectively contribute to the characteristics of the population. In particular, virus populations have been called quasispecies to indicate their extensive genetic heterogeneity. Viral quasispecies evolution refers to the fact that RNA viral populations consist of mutant spectra (or mutant clouds) rather than genomes with the same nucleotide sequence. In other words, mutant spectra and not individual genomes may be the target of evolutionary events. It is suggested that this quasispecies evolution would allow the organism to maximize its potential to respond to changing environments, thus allowing any given quasispecies in the cloud to survive detrimental conditions, such as aggressive antiviral or antibacterial treatments. By detecting the varied quasispecies present in the mutant cloud, diagnostic tools can enable truly precise personal medical treatments.

DETAILED DESCRIPTION

Techniques disclosed herein generally relate to identifying phased variants and identifying quasispecies based on the phased variants in long sequence reads. More specifically, in one embodiment, an improve method is provided for identifying quasispecies of samples with high sensitivity by clustering long sequence reads for samples based on the similarities in the phased variants among the long sequence reads. In yet another embodiment, a dynamic programming strategy is implemented for choosing the node to cut a hierarchal tree generated by the clustering. An objective function that minimizes the cost between a given node and the sum of its children nodes may be used in dynamic programming strategy, where the cost of a node may be, for example, the intra-cluster Hamming distance.

Recent advances in genome sequencing technologies provide unprecedented opportunities to characterize individual genomic landscapes and identify mutations relevant for diagnosis and therapy. With the large amount of data produced by next-generation sequencing (NGS) technologies, the possibility of predicting the functional impact of variants in an automated fashion is becoming possible. Computer-aided annotation enables research groups to filter and prioritize potential disease-causing mutations for further analysis. The available tools implement different methods for variant annotation. Most of available tools focus on the annotation of single nucleotide polymorphisms (SNPs) as independent events.

However, many research results and findings indicate that relationships between DNA sequence and phenotype, including disease, can be more fully understood with phase information. Thus, there has been increased interest to understand the importance of co-occurring SNPs (phased variants) that may exist on a subpopulation or a subset of the sample being analyzed. For example, in some cases, some patients having a type of disease (e.g., human immunodeficiency virus (HIV)) may respond to a drug, but some patients having the same type of disease may not respond to the same drug, at least at some time. Thus, it is likely that there is a subpopulation (i.e., quasispecies) in the virogenomes that has a different mutation profile that may allow a virus to respond to a drug differently. Detection of such subpopulation or quasispecies, if any, in mixed viral samples may better inform drug regimens for patients with complex infections by targeting both major and minor populations.

Long read next-generation sequencing may enable phasing across long distance genomic scales without relying on trio analysis or statistical inference. By identifying haplotype information, phased sequencing may inform studies of complex traits, which are often influenced by interactions among multiple genes and alleles. Phasing may also provide valuable information for genetic disease research, as disruptions to alleles in cis or trans positions on a chromosome can cause some genetic disorders. Phasing may also help researchers to analyze compound heterozygotes, measure allele-specific expression, and identify variant linkage.

Many techniques have been developed to impute the phasing of detected SNPs for short read sequencing technology. With the advent of long-read sequencing technology, such as techniques provided by Pacific Biosciences or Oxford Nanopore, it is possible to directly detect phased variants. For example, a Long-Amplicon Analysis (LAA) technique that takes advantages of the long sequence reads to determine the subpopulations of phased information within a sample may be used to cluster entire read sequences based on their similarities. However, because current long sequence reads are more susceptible to noise, the LAA method may have limited sensitivity and accuracy. Furthermore, because a long sequence read may have a large number of bases (e.g., several thousand or more) that may vary from a reference sequence, it may be difficult and time consuming to cluster directly using the long sequence reads.

Embodiments can overcome such problems by, for example, using a variant matrix with only qualified mutations (variants).

In some embodiments of the techniques disclosed herein, nucleotide differences (i.e., mutations, also referred to as variants) between the long sequence reads and a reference sequence are captured. A variant matrix is generated based on the differences in reads. Each row (or column) of the variant matrix may include a single long sequence read, and each column (or row) of the variant matrix may correspond to a variant that passed quality checks (e.g., greater than a depth of read threshold and a frequency of occurrence threshold). Hierarchical clustering can then be used to find groups of reads (rows or columns) that carry similar mutation patterns based on the variant matrix. The resultant tree structure from the hierarchical clustering may be cut to separate reads into disjoint groups that may constitute quasispecies. The cutting of the true structure may be performed by, for example, minimizing intra-cluster differences using dynamic programming.

The disclosed method may be applicable to any sequencing data and/or application using the phasing information of SNPs. Potential applications may include, for example, detecting quasispecies in biological samples and population-aware error correction that can expand variant detection limit (e.g., over 1%).

I. Detecting Quasispecies

As described above, it may be important to determine phased variants that may exist on a subpopulation or a subset of organisms in the sample being analyzed. For example, there might be a subpopulation in the viro-genomes that has a different mutation profile that may allow a virus to respond to a drug differently. Detection of such subpopulation may better inform drug regimens for patients with complex infections by targeting both major and minor populations. Due to more noises on long sequence reads and difficulty in clustering long sequence reads that may have many bases (e.g., 30 kilobases (kb)), a more accurate and efficient method may be needed to identify subpopulations based on long sequence reads.

FIG. 1 is a flow chart 100 illustrating an example method of identifying quasispecies based on phased variants in long sequence reads, according to certain aspects of the present disclosure. In the example method, a variant matrix that includes variants that have passed a quality check may be generated and used for clustering. Thus, noises from the long sequence reads may be filtered out, and a matrix that is much smaller than all the long sequence reads may be used to more efficiently and accurately cluster the reads and identify subpopulations.

At block 110, one or more samples including multiple organisms having different but related genomes (e.g., different subspecies of a bacteria or virus, or different variant alleles of human DNA) may be obtained. The samples may include any biological or environmental samples containing or presumed to contain nucleic acid, as described above. In one example, the samples may be collected from patients having a same type of disease, such as, for example, HIV, lung cancer, breast cancer, colon cancer, etc.

At block 120, long sequence reads for the one or more samples may be obtained, for example, by performing long-read sequencing or assembling short sequence reads. Each of the long sequence reads may include, for example, at least 1000 bases (e.g., about 30 kb) and at least 2 (e.g., about 100) variant loci at which different genomes may have different alleles.

At block 130, a variant matrix may be generated based on the long read sequences and a reference sequence. Each of the row (or column) of the variant matrix may correspond to a single long read sequence and every column (or row) of the variant matrix may represent a variant that passes quality check. The variant matrix may include a much lower number of columns (or rows) than the number of bases in each long sequence read. Thus, the complexity for clustering may be reduced. Detailed techniques for generating the variant matrix are described in Section III of this disclosure.

At block 140, a hierarchy of clusters for the plurality of rows (or columns) of the variant matrix may be generated based on the differences among the plurality of rows (or columns) of the variant matrix. The results of the hierarchical clustering of the long read sequences may be presented in, for example, a tree structure, such as a row (or column) dendrogram. Detailed techniques for generating the hierarchy of clusters for the long read sequences are described in Sections IV of this disclosure.

At block 150, the hierarchy of clusters (tree structure) may be cut to identify clusters as different quasispecies of the genomes. Detailed techniques for cutting the hierarchy of clusters to identify clusters as different quasispecies of the genomes are described in Section V of this disclosure.

At block 160, the identified quasispecies may optionally be used to perform disease diagnosis and/or treatment. For example, drugs targeted at a particular virus of a particular quasispecies may be used to treat a patient that has been infected by the particular virus. The diagnostic information may also be used in an epidemiology study to trace and understand viral evolution in a given patient or across populations. In another example, the diagnostic information may be used to understand the evolution of super viruses under environmental stresses of antiviral treatments.

Example results using techniques disclosed herein are described in Section VI of this disclosure.

II. Long-Read Sequencing and Phasing of Genetic Variants

The sequences of biological samples can be obtained from many sources (public or private) in a suitable manner. The sequences can be obtained using any suitable sequencing technique.

While the identification of individual SNPs has been readily available for some time, the ability to accurately phase SNPs and structural variations across a haplotype has been a challenge. Several technologies, such as techniques developed by Pacific Biosciences or Oxford Nanopore, may be used for genuine rather than synthetic long-read sequencing. See, e.g., Flusberg et al., Nat Methods 2010; 7: 461-465; Greninger et al., "Rapid metagenomic identification of viral pathogens in clinical samples by real-time nanopore sequencing analysis," Genome Medicine 2015 7:99; and Jain et al., "The Oxford Nanopore MinION: delivery of nanopore sequencing to the genomics community," *Genome Biology* 2016 17:239.

Long amplicon analysis (LAA) can directly take long read sequences and identify and report the abundance of differing clusters of sequencing reads within a single library. With individual reads of up to, for example, 30 kb in length, LAA method allows the identification of combinations of mutations, such as microdeletions, insertions, and substitutions, without any predetermined reference sequence. For example, the long reads can be compared to each other, thereby obviating the need for a predetermined reference sequence. Graphs generated via hierarchical clustering of individual sequence reads can then be used to generate Markov models representing the consensus sequence of individual clusters found to be significantly different. Long amplicon analysis is capable of differentiating between underlying sequences that are similar, such as haplotypes and pseudogenes. Long amplicon analysis allows for the elucidation of complex regions otherwise missed by other methodologies, which may contribute to the diagnosis and understanding of otherwise mysterious diseases.

FIG. 2 illustrates example sequence reads in a sequence matrix 200. Sequence matrix 200 may include M long sequence reads 220 aligned to a reference sequence 210, where M may be more than a few hundred, more than a few thousand, or more than tens of thousands. Each long sequence read may be represented by a row in sequence matrix 200. Each long sequence read may include N bases, where N may be more than 1000, 5000, 10,000, 30,000, 60,000, or more. Therefore, sequence matrix 200 may include more than a few millions of elements. The many elements of sequence matrix 200 contrasts with mutation matrices discussed below.

Some long sequence reads 220 may include no variants compared with reference sequence 210, while most long sequence reads 220 may include one or more variants at one or more loci compared with reference sequence 210. For example, some long sequence reads 220 may include, for example, 0.1% or less, 0.3% or less, 0.5% or less variants out of the N bases compared with reference sequence 210. At some loci, different long sequence reads 220 may have different alleles (variants) at a same locus. At some loci, there may be no variants or a low number of variants for all long sequence reads.

III. Variant Matrix

As described above, sequence matrix 200 may include millions of elements. Thus, it may be difficult and time consuming to cluster the long sequence reads based on all the elements in sequence matrix 200. In addition, many of the variants in sequence matrix 200 may be caused by errors during the sequencing, and/or many loci may not have any variants for any sequence reads. Therefore, a large amount of the data in sequence matrix 200 may not be useful for the clustering.

According to certain embodiments, a variant matrix may be generated based on the long sequence reads and the reference sequence. The variant matrix may only include variants that have passed a quality check, and thus may include a much lower number of columns than the number of bases in each long sequence read. The quality check may include one or more criteria, for example, the depth of reads and the frequency of occurrence (e.g., a number of long sequence reads having the particular variant).

Figure 3:
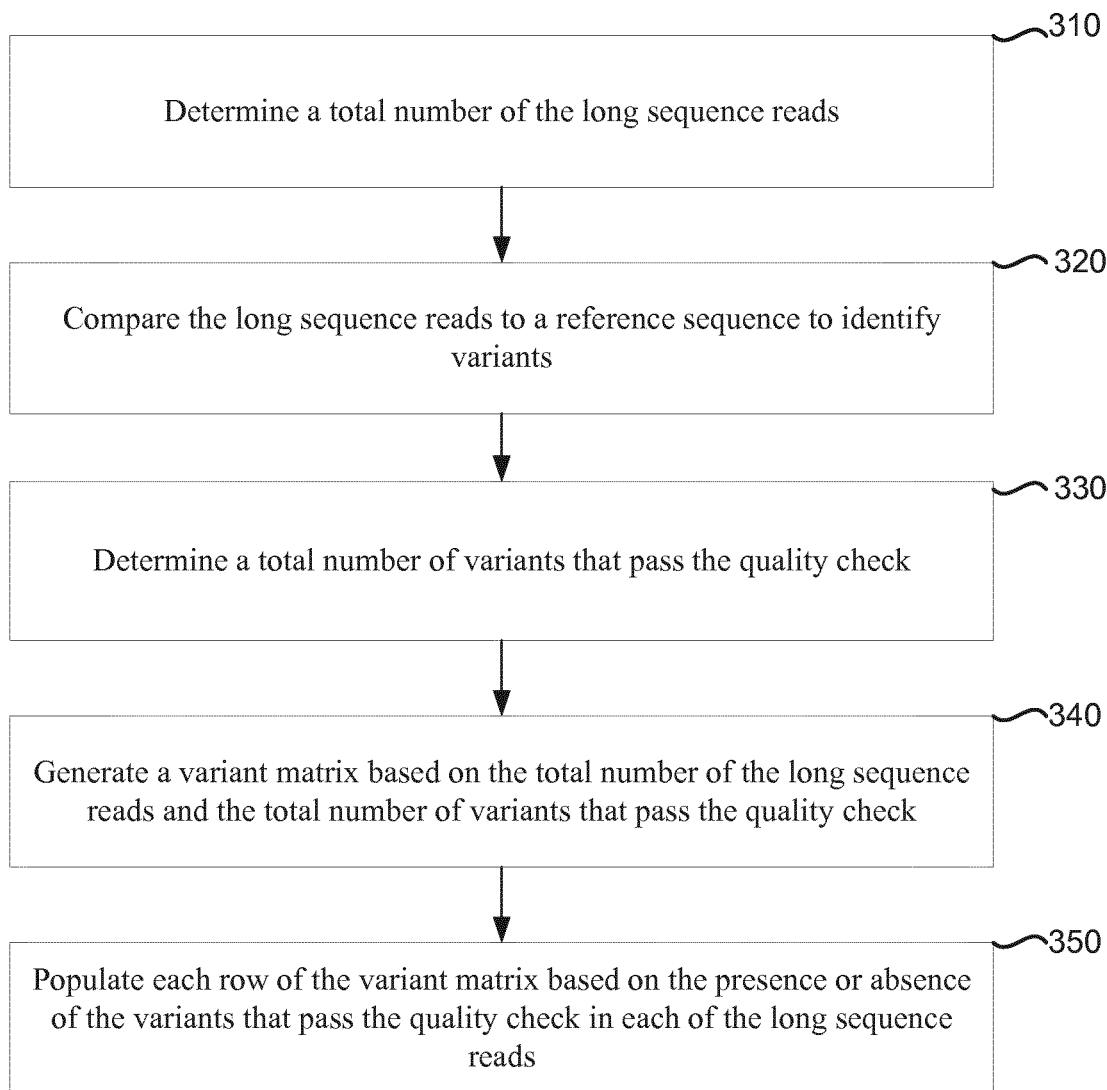
FIG. 3 is a flow chart illustrating an example method of generating a variant matrix for clustering based on long sequence reads, according to certain aspects of the present disclosure.

FIG. 3 is a flow chart 300 illustrating an example method of generating a variant matrix for clustering based on long sequence reads, according to certain aspects of the present disclosure. The variant matrix may be generated using any suitable long read sequencing technology, followed by suitable sequence aligner (i.e. bwa, bowtie2, etc.) and variant caller (e.g. samtools, GATK etc.). See, e.g., http://bio-bwa.sourceforge.net/; http://bowtie-bio.sourceforge.net/bowtie2/index.shtml; http://samtools.sourceforge.net/; http://www.htslib.org/; and https://software.broadinstitute.org/gatk/.

At block 310, a total number of long sequence reads may be determined. Some sequence reads may be discarded at this stage. For example, some sequence reads may have excessive number of variants that might be caused by sequencing errors and not by the underlying sequence of the nucleic acid, or some sequence reads might not align with the reference sequence.

At block 320, each of the long sequence reads may be compared against the reference sequence to identify variants. A variant may include any difference between two sequences at a locus, such as, for example, a change of one base to one or more other bases, an insertion of one or more bases, or a deletion of one or more bases.

At block 330, a total number of variants that pass a quality check may be determined. As described above, some of the variants may be caused by, for example, errors during the sequencing process, which may be randomly distributed among all bases. Thus, the frequency of occurrence for these variants caused by sequencing errors may be lower than a frequency of occurrence of a valid variant. One may desire to filter against all variants occurring at a rate lower than the noise floor of the sequencing technology. In some cases, a variant may be detected at a locus where there may not be sufficient number of reads. Such variants may be removed or discarded from the variants identified at block 320.

At block 340, a variant matrix may be generated based on the total number of long sequence reads determined at block 310 and the total number of variants that pass the quality check determined at block 330. As discussed above, multiple variants may occur at a same locus. Therefore, the total number of columns to represent all the variants may be larger than the number of loci with an observed variant.

At block 350, each row of the variant matrix may be populated based on the presence or absence of the variants that pass the quality check in each of the long sequence reads. The presence or absence of the variants may be indicated by a single bit binary number, such as zero or one. In some implementations, the variants at a locus may be represented by a binary number with two or more digits. For example, if there are three different variants at a locus, the variants may be indicated by a two-digit number, where "00" may indicate that a variant does not exist on a particular long sequence read, "01" may indicate a first variant (e.g., A>G) on a long sequence read, "10" may indicate a second variant (e.g., A>T) on another long sequence read, and "11" may indicate a third variant (e.g., a deletion) on a different long sequence read.

Figure 4:
FIG. 4 illustrates an example variant matrix for long sequence reads, according to certain aspects of this disclosure.

FIG. 4 illustrates an example variant matrix 400 for long sequences reads, such as the long sequence reads shown in sequence matrix 200 of FIG. 2, according to certain aspects of this disclosure. Variant matrix 400 may include M' long sequence reads, each represented by a row, where M' may be determined at block 310 of FIG. 3 and may be equal to or less than M in sequence matrix 200. Variant matrix 400 may include N' variants each represented by a column, where N' may be determined at block 330 of FIG. 3 and may be much smaller than N in sequence matrix 200, such as 100 or less. As such, the number of elements in variant matrix 400 may be much lower than the number of elements in sequence matrix 200, and it may thus be much easier to cluster the M' long sequence reads based on variant matrix 400. As described above, more than one valid variant may occur on two or more sequence reads at a locus, such as, for example, loci 1 and 25 in variant matrix 400, where v1, v2, and v3 may indicate different variants.

As an example, the mutations on sequence read 1 with respect to a reference sequence may be represented by row 410 in variant matrix 400. A "1" at locus 5 indicates that a valid variant (variant that passes the quality check) (e.g., C>A) occurs at locus 5 in sequences read 1. A "1" at v2 of locus 25 indicates that sequence read 1 has a variant v2 at locus 25. For example, the base at locus 25 on the reference sequence may be A, v1 may represent a variant A>C at locus 25, v2 may represent a variant A>G at locus 25, and v3 may represent a deletion of base A at locus 25. Thus, row 410 of variant matrix 400 may indicate that sequence read 1 has a variant A>G at locus 25. A "0" at a locus in row 410, for example, locus 1, 10, 42, etc., indicates that the base at the locus on sequence read 1 is the same as the base at the locus on the reference sequence.

In some implementations, prior to starting the clustering process, identical rows in the variant matrix may be collapsed. The indices of the collapsed rows may be recorded for later use, such as tracking for debugging purposes or for final counting.

IV. Hierarchical Clustering

Hierarchical clustering (also called hierarchical cluster analysis (HCA)) seeks to build a hierarchy of clusters. Strategies for hierarchical clustering generally fall into two types: agglomerative clustering and divisive clustering. Agglomerative clustering is a "bottom up" approach, where each observation (e.g., long sequence read) may start in its own cluster, and pairs of clusters are merged as one moves up the hierarchy. Divisive clustering is a "top down" approach, where all observations start in one cluster, and splits are performed recursively as one moves down the hierarchy. In general, the merges and splits can be determined in a greedy manner.

The results of hierarchical clustering can be presented in a dendrogram. In order to decide which clusters should be combined (for agglomerative), or where a cluster should be split (for divisive), a measure of dissimilarity (or similarity) between sets of observations can be determined. The measure of dissimilarity between sets of observations may be achieved by use of an appropriate metric (e.g., a measure of distance between pairs of observations), and a linkage criterion that specifies the dissimilarity of sets as a function of the pairwise distances of observations in the sets.

For example, one agglomerative method may build the hierarchy of clusters from the individual reads by progressively merging clusters. A distance matrix may be constructed using distances between reads. The distance value in the i-th row and j-th column of the distance matrix may represent the distance between the i-th read and the j-th read. As examples, the distance may be a correlation, a cosine correlation, a Hamming distance, a Tanimoto coefficient, an Euclidean distance, a city block distance, a square Euclidean distance, a half square Euclidean distance, etc. As clustering progresses, rows (or columns) may be merged as the clusters are merged, and the distances are updated. The distance between two clusters A and B may be determined based on, for example, the minimum distance between reads (x and y) of each cluster: $\min\{d(x, y): x \in A, y \in B\}$. Other values can be used as well, such as the average distance or a maximum distance. The clustering may end when the clusters are merged such that there is a sufficiently small number of clusters (e.g., 3 or less) at the top level of the hierarchy according to a number criterion, or when the clusters are too far apart to be merged according to a distance criterion, e.g., a threshold.

Figure 5:
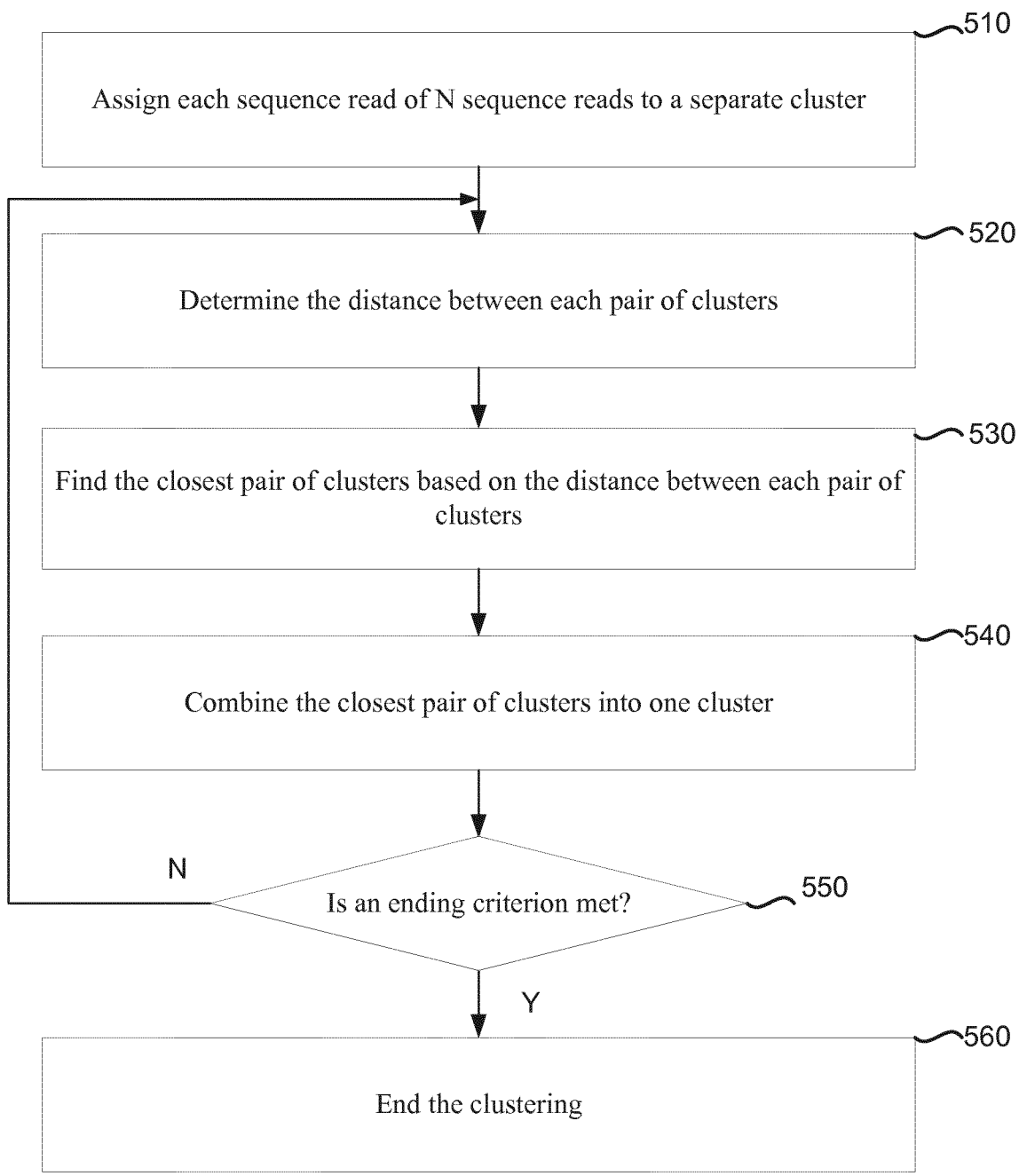
FIG. 5 is a flow chart illustrating an example method of generating a hierarchy of clusters based on long sequence reads, according to certain aspects of the present disclosure.

FIG. 5 is a flow chart 500 illustrating an example method of generating a hierarchy of clusters based on long sequence reads, according to certain aspects of the present disclosure.

At block 510, given a set of N sequence reads to be clustered, an agglomerative clustering method may assign each sequence read of N sequence reads to a separate cluster. The separate clusters can be represented as rows or columns of a matrix.

At block 520, a distance between each pair of clusters may be determined. One example of the distance between a pair of sequence read may be a Hamming distance, which may be the number of positions at which each pair of sequence reads are different, or the minimum number of substitutions required to change one sequence read into the other sequence read. In some implementations, the distance measure between two clusters may be calculated as $D=1-C$, where D is the distance and C is the correlation (e.g., a Pearson correlation coefficient) between clusters. If two clusters are highly correlated, they will have a correlation value close to 1, thus $D=1-C$ will have a value close to zero. Clusters that are not correlated may have a correlation value of zero, and thus a corresponding distance value of 1. Clusters that are negatively correlated (e.g., showing opposite abundance behavior) may have a correlation value of $-1$, and thus a distance of $D=1-(-1)=2$.

Operations at block 520 may be done in different ways for different clustering methods, such as single-link clustering, complete-link clustering, and average-link clustering. For example, in single-link clustering (also referred to as connectedness or minimum method), the distance between one cluster and another cluster may be calculated as the shortest distance from any member of one cluster to any member of the other cluster. In complete-link clustering (also referred to as the diameter or maximum method), the distance between one cluster and another cluster may be calculated as the longest distance from any member of one cluster to any member of the other cluster. In average-link clustering, the distance between one cluster and another cluster may be calculated as the average distance from any member of one cluster to any member of the other cluster.

At block 530, the closest pair of clusters (i.e., the pair of clusters with the shortest distance) may be determined based on the distances between each pair of clusters. The smallest value for the distances can be identified in a variety of ways. For example, a sorted list can be kept as each distance is determined. As another example, a final list can be searched element by element to determine the smallest value.

At block 540, the closest pair of clusters may be combined into one cluster. Whether the closest pair of clusters are combined can depend on a distance criterion.

At block 550, it may be determined whether an ending criterion is met. The ending criterion may be, for example, the number criterion or the distance criterion described above. If the ending criterion is not met, the clustering method may repeat the operations at blocks 520-540 using the updated clusters until the ending criterion is met. After the ending criterion is met, the clustering may end.

The hierarchical clustering can arrange items in a hierarchy with a tree-like structure, such as a dendrogram, based on either the distance or the similarity between them. A dendrogram is a visual representation of the compound correlation data, and may be presented with heat map visualization. Rows and columns of the heat map can be clustered to form row or column dendrogram. The clusters may be formed by joining individual sequence reads or existing clusters of sequence read, where the join point may be referred to as a node. A row dendrogram may show the distance or similarity between rows, and which nodes each row belongs to as a result of clustering. A column dendrogram may show the distance or similarity between different variables (such as different variants in the sequence reads or different genes).

Figure 6:
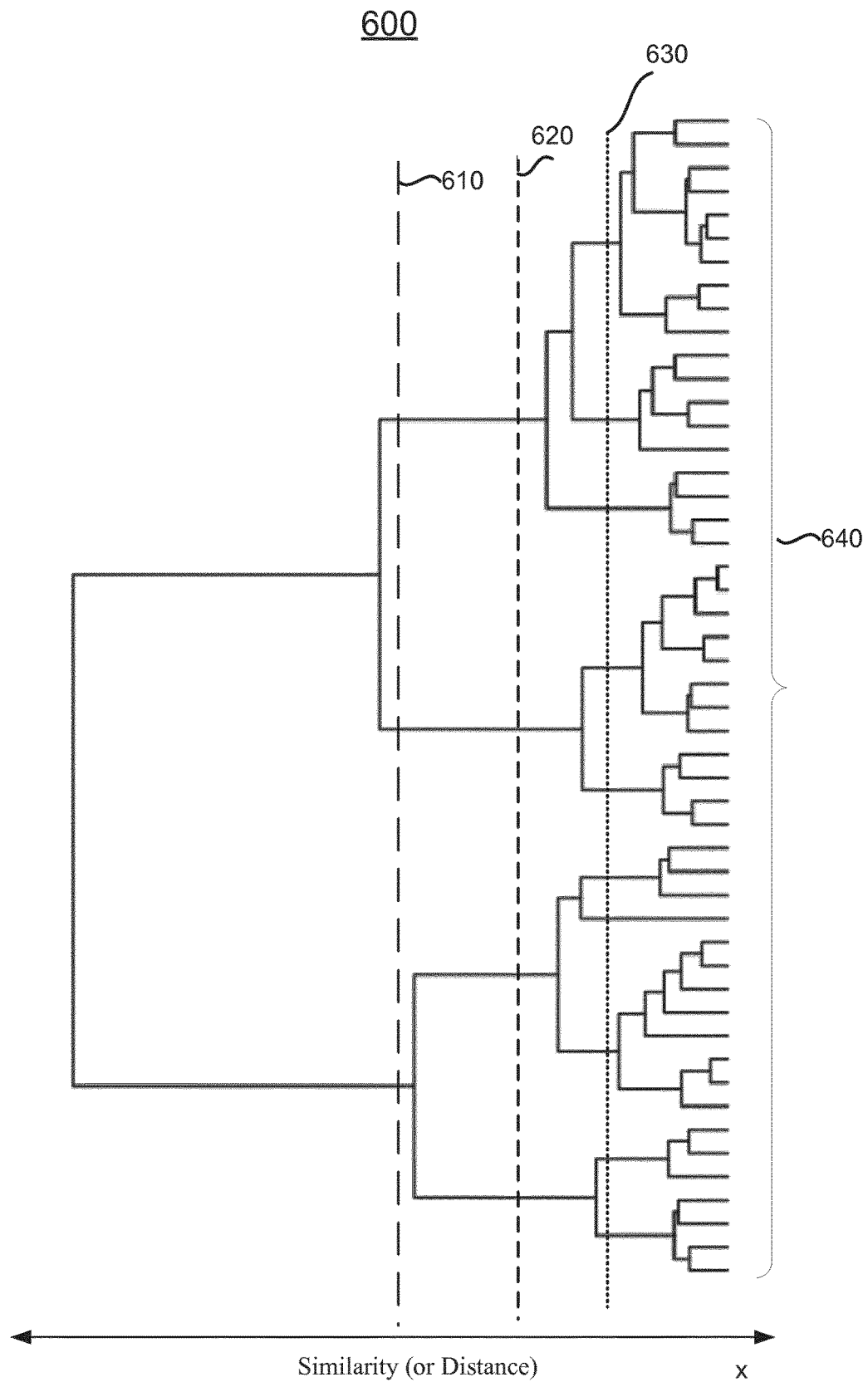
FIG. 6 illustrates an example dendrogram, according to certain aspects of this disclosure.

FIG. 6 illustrates an example row dendrogram 600, according to certain aspects of this disclosure. The individual rows (representing long sequence reads) in the clustered data may be represented by the right-most nodes 640 (i.e., the leaf nodes) in the row dendrogram. Each node in the dendrogram represents a cluster of all rows that lie to the right of it in the dendrogram. The left-most node in the dendrogram is therefore a cluster that contains all rows. In some implementations, the x-axis in the dendrogram may indicate the distances or similarities at the nodes.

V. Quasispecies Identification

To identify subpopulations or quasispecies, the hierarchy of clusters (e.g., a hierarchical tree, such as a dendrogram) may be cut based on different criteria. Cutting the dendrogram may be referred to as tree cutting or branch pruning Cutting at different distance levels may give different sets of clusters. For example, FIG. 6 show three different pruning lines 610, 620, 630 at different distance levels. Cutting at pruning line 610 may generate three clusters, cutting at pruning line 620 may provide four clusters, and cutting at pruning line 630 may provide 10 clusters.

Various techniques may be used to find the optimum cutting level. Traditional methods of presetting the expected number of final clusters or the distance threshold yield are non-ideal for addressing real world samples, which may vary dramatically from sample to sample. As shown in FIG. 6, the traditional methods may force a selection along an arbitrary vertical line through the dendrogram. According to certain aspects of the present disclosure, an alternative dynamic programming method that uses an objective function, which seeks to minimize the cost at each node, may allow for a more responsive approach.

Figure 7:
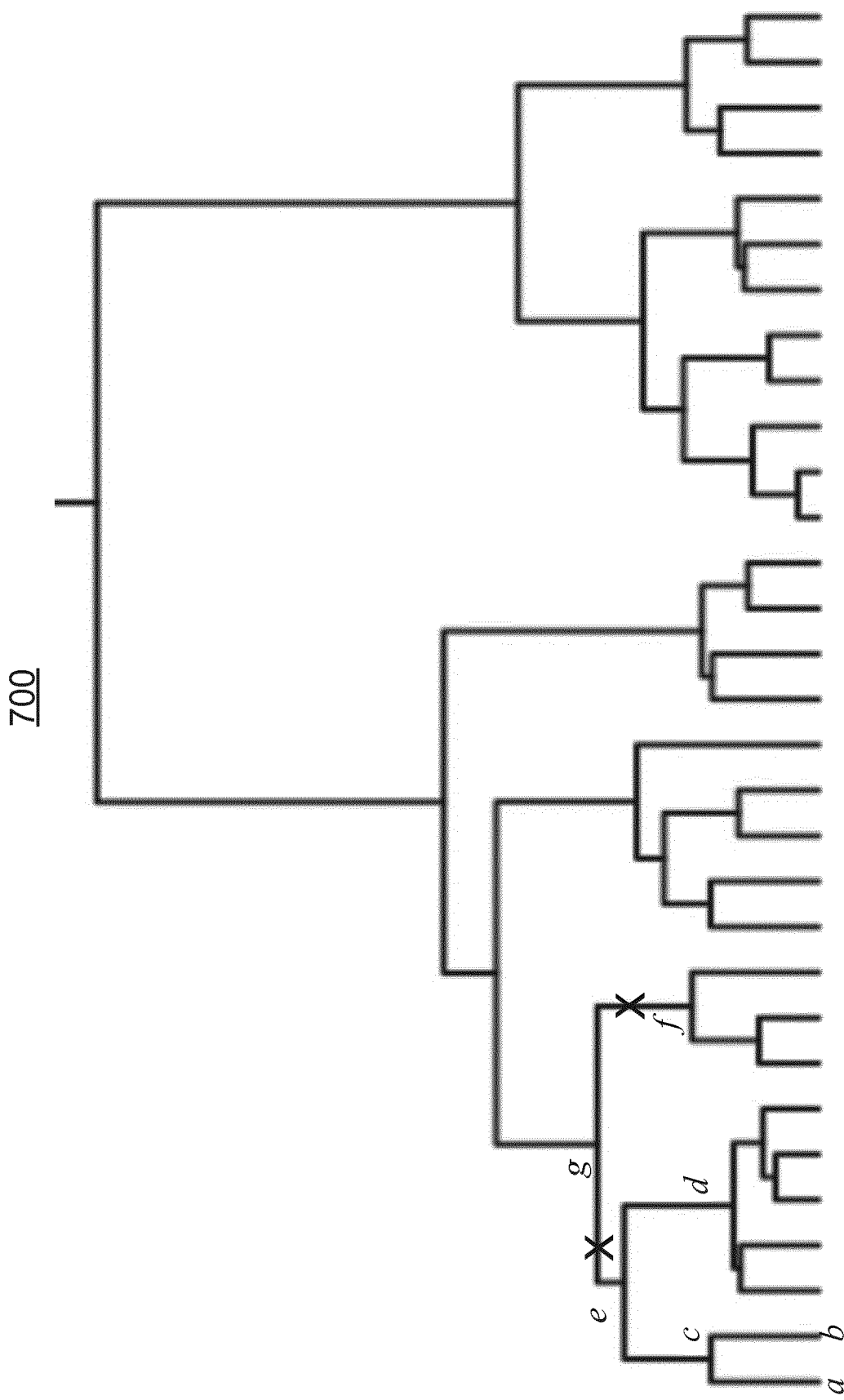
FIG. 7 illustrates an example dynamic programming method for finding the optimum cutting level for a hierarchical tree, according to certain embodiments.

FIG. 7 illustrates an example dynamic programming method for finding the optimum cutting level for a hierarchical tree 700 (e.g., a dendrogram), according to certain embodiments. In the example dynamic programming method shown in FIG. 7, the optimum cutting level for hierarchical tree 700 may be selected to minimize the cost $OPT(u)$ at a given non-leaf node u by solving the following equation:

$$OPT(u) = \min\{Q(u), OPT(v) + OPT(w)\}, \quad (1)$$

where u is a non-leaf node in the tree, v and w are the children nodes of u, $OPT(v)$ is the cost of node v, $OPT(w)$ is the cost of node w, and $Q(u)$ is the quality value of merging all leaf nodes under node u into a single cluster. In one example, the quality value of a node u may be the intra-cluster Hamming distance between all reads under node u. For example, if nodes v and w are leaf nodes, $OPT(v)$ may be the same as $Q(v)$ and may represent the average Hamming distance between all the reads under node v, $OPT(w)$ may be the same as $Q(w)$ and may represent the average Hamming distance between all the reads under node w, $Q(u)$ may be the average Hamming distance between all reads under node u, and the cost $OPT(u)$ of node u may be determined based on $OPT(v)$, $OPT(v)$, and $Q(u)$ using Equation 1.

In some embodiments, the dynamic programming method may start from the bottom of each branch of the tree and move up the tree along the branch. At each non-leaf node u, if $Q(u)$ is no greater than the sum of the costs $OPT(v)$ and $OPT(w)$ of its child nodes v and w, then the tree would not be cut at nodes below node u. In other words, child nodes v and w would not be treated as separate sub-clusters or subspecies. The cost $OPT(u)$ of node u may then be set to the quality value $Q(u)$ of node u, and the tree cutting process may move up the tree along the branch to the parent node of node u to determine the cost of the parent node of node u using Equation 1. If $Q(u)$ is greater than the sum of $OPT(v)$ and $OPT(w)$, $OPT(u)$ may be set to the sum of $OPT(v)$ and $OPT(w)$, the tree may be cut at nodes v and w, and the tree cutting process may terminate for the branch. In other words, nodes v and w may be determined to be separate sub-clusters or subspecies.

The example tree cutting process shown in FIG. 7 may start at leaf nodes a and b. The costs of nodes a and b may be determined to be $OPT(a)$ (or $Q(a)$) and $OPT(b)$ (or $Q(b)$), respectively. The quality value of the parent node c of nodes a and b may be determined to be $Q(c)$ based on the average Hamming distance between all reads under node c. $Q(c)$ may be compared with the sum of $OPT(a)$ and $OPT(b)$ according to Equation 1. If $Q(c)$ is greater than the sum of $OPT(a)$ and $OPT(b)$, $OPT(c)$ may be set to the sum of $OPT(a)$ and $OPT(b)$ according to Equation 1, the tree may be cut at nodes a and b, and the tree cutting process for the current branch may terminate. In the example shown in FIG. 7, $Q(c)$ is less than the sum of $OPT(a)$ and $OPT(b)$. Thus, $OPT(c)$ may be set to $Q(c)$ according to Equation 1, and the tree cutting process may continue by moving up to the parent node e of the node c. The cost $OPT(d)$ of child node d of node e may be determined similarly using Equation 1.

At node e, the cost $OPT(e)$ of node e may be determined based on Equation 1, $OPT(a)$ and $OPT(b)$, and the quality value $Q(e)$ of node e, which may represent the average Hamming distance between all reads under node e. If $Q(e)$ is greater than the sum of $OPT(c)$ and $OPT(d)$, $OPT(e)$ may be set to the sum of $OPT(c)$ and $OPT(d)$ according to Equation 1, the tree may be cut at nodes c and d, and the tree cutting process for the current branch may terminate. In the example shown in FIG. 7, $Q(e)$ is less than the sum of $OPT(c)$ and $OPT(d)$. Thus, $OPT(e)$ may be set to $Q(e)$ according to Equation 1, and the tree cutting process may continue by moving up to the parent node g of the node e. The cost $OPT(t)$ of child node f of node g may be determined similarly using Equation 1.

At node g, the cost $OPT(g)$ of node g may be determined based on Equation 1, $OPT(e)$ and $OPT(f)$, and the quality value $Q(g)$ of node g, which may be the average Hamming distance between all reads under node g. If $Q(g)$ is no greater than the sum of $OPT(e)$ and $OPT(f)$, $OPT(g)$ may be set to $Q(g)$ according to Equation 1, and the tree cutting process may continue by moving up to the parent node of node g. In the example shown in FIG. 7, $Q(g)$ is greater than the sum of $OPT(e)$ and $OPT(f)$. Thus, $OPT(g)$ may be set to the sum of $OPT(e)$ and $OPT(f)$ according to Equation 1, the tree may be cut at nodes e and f, and the tree cutting process for the current branch may terminate. Thus, all reads under node e may be determined to be from a sub-cluster or subspecies, and all reads under node f may be determined to be from another sub-cluster or subspecies.

Figure 8:
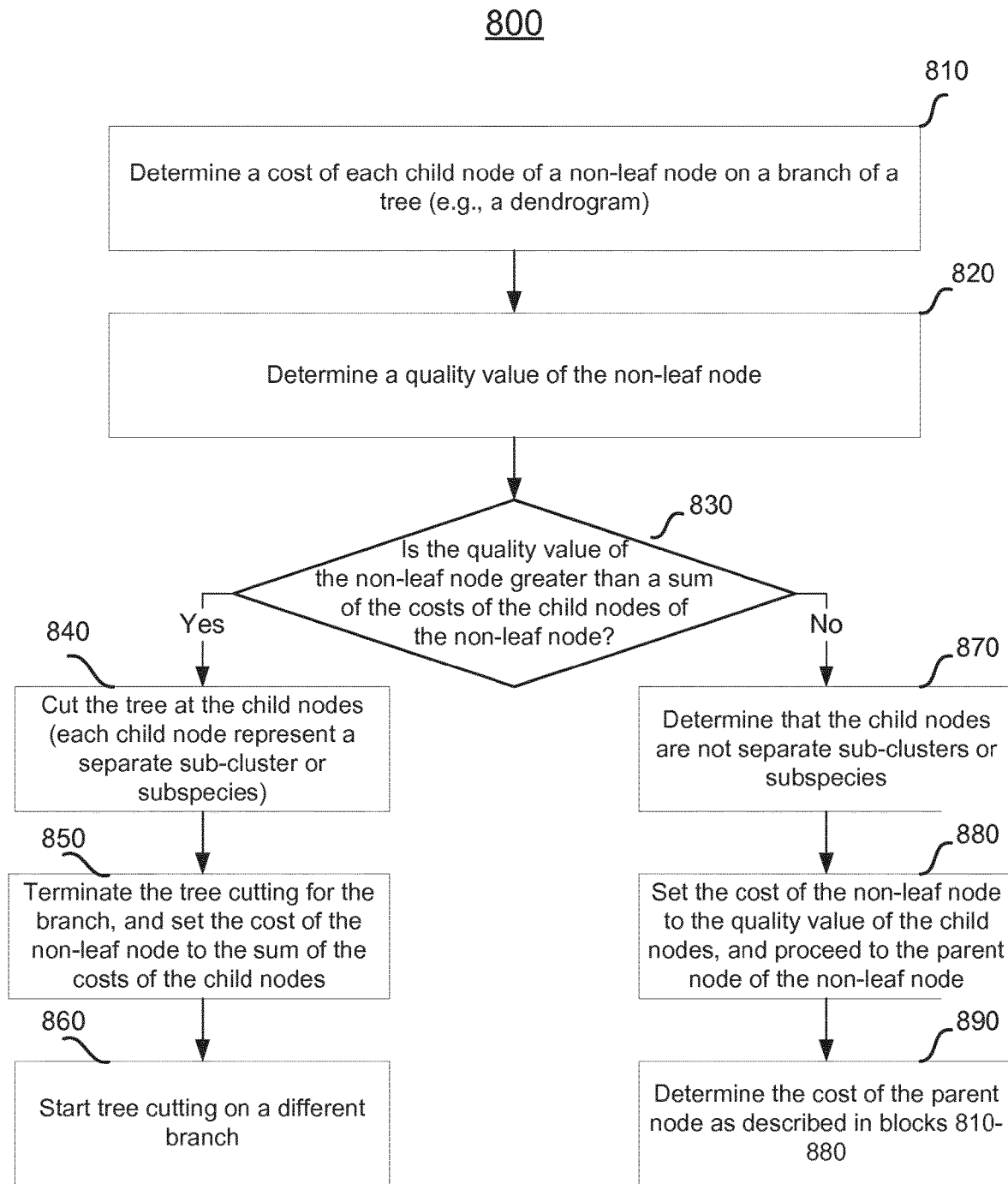
FIG. 8 is a flow chart illustrating an example method for cutting a dendrogram to identify quasispecies, according to certain aspects of this disclosure.

FIG. 8 is a flow chart 800 illustrating an example method for cutting a tree (e.g., a dendrogram) to identify quasispecies, according to certain aspects of this disclosure. The method may be performed at any non-leaf node of the tree, and may be performed recursively from the non-leaf node(s) at the bottom of a branch of the tree to the non-leaf node(s) at the top of the branch until the cutting locations (nodes) are determined. In some implementations, the method described with respect to FIG. 8 may be performed concurrently on multiple branches of the tree.

At block 810, a cost of each child node of a non-leaf node on a branch of a tree may be determined. If a child node is a leaf node, the cost of the child node may be the quality value of the child node, which, in some implementations, may be the average distance (e.g., Hamming distance or Euclidean distance) between all reads under the child node. In some implementations, the quality value of a node may be the correlation between all reads under the node. If a child node of the non-leaf node is also a non-leaf node, the cost of the child node may be determined using the method described with respect to flow chart 800 based on the costs of the child nodes of the child node.

At block 820, a quality value of the non-leaf node may be determined. In some implementations, the quality value of the non-leaf node may be the average distance (e.g., Hamming distance or Euclidean distance) between all reads under the non-leaf node. In some implementations, the quality value of the non-leaf node may represent the correlation between all reads under the non-leaf node.

At block 830, the quality value of the non-leaf node may be compared with a sum of the costs of the child nodes of the non-leaf node. If the quality value of the non-leaf node is greater than the sum of the costs of the child nodes of the non-leaf node, the flow may proceed to block 840. Otherwise, the flow may proceed to block 870.

At block 840, the tree may be cut at the child nodes such that each child node may be determined to be a separate sub-cluster or subspecies (or quasispecies). At block 850, the tree cutting process for the branch may be terminated, and optionally, the cost of the non-leaf node may be set to the sum of the costs of the child nodes. At block 860, the tree cutting process may be started on a different branch of the tree.

At block 870, it may be determined that the child nodes are not separate sub-clusters or subspecies. Thus, the tree would not be cut at a level below the non-leaf node. At block 880, the cost of the non-leaf node may be set to the quality value of the non-leaf node, and the tree cutting process may proceed to the parent node of the non-leaf node. At block 890, the cost of the parent node may be determined in a way similar to the method described in blocks 810-880.

Even though FIG. 8 describes the example method as sequential operations, some of the operations may be performed in parallel or concurrently. For example, operations at block 810 and 820 may be performed in parallel. Some operations may be performed in a different order. An operation may have additional steps not included in the figure. Some operations may be optional, and thus may be omitted in various embodiments. Some operations may be performed together with another operation. Furthermore, embodiments of the methods may be implemented in hardware, software, firmware, middleware, microcode, hardware description languages, or any combination thereof.

VI. Example Results

The disclosed techniques have been applied to data samples for various types of genomes, and some example experiment results are described below. In the experiments, sequence reads from wild type and sequence reads from samples having different mutation rates (e.g., 0.3% and 0.5%) are classified. A precision value and recall value of the classification can be determined, and an F1 measure can be determined based on the precision and recall. As used herein, the precision (also called positive predictive value) may be defined as the fraction of true positive calls over all positive calls, and the recall (also known as sensitivity) may be defined as the fraction of true positive call over the sum of the true positive call and false negative calls. The F1 measure is a measure of a test's accuracy and may be defined as the harmonic mean of precision and recall, e.g., $$F=2(\text{Precision} \times \text{Recall})/(\text{Precision}+\text{Recall}). \qquad (2)$$

Figures 9A, 9B:
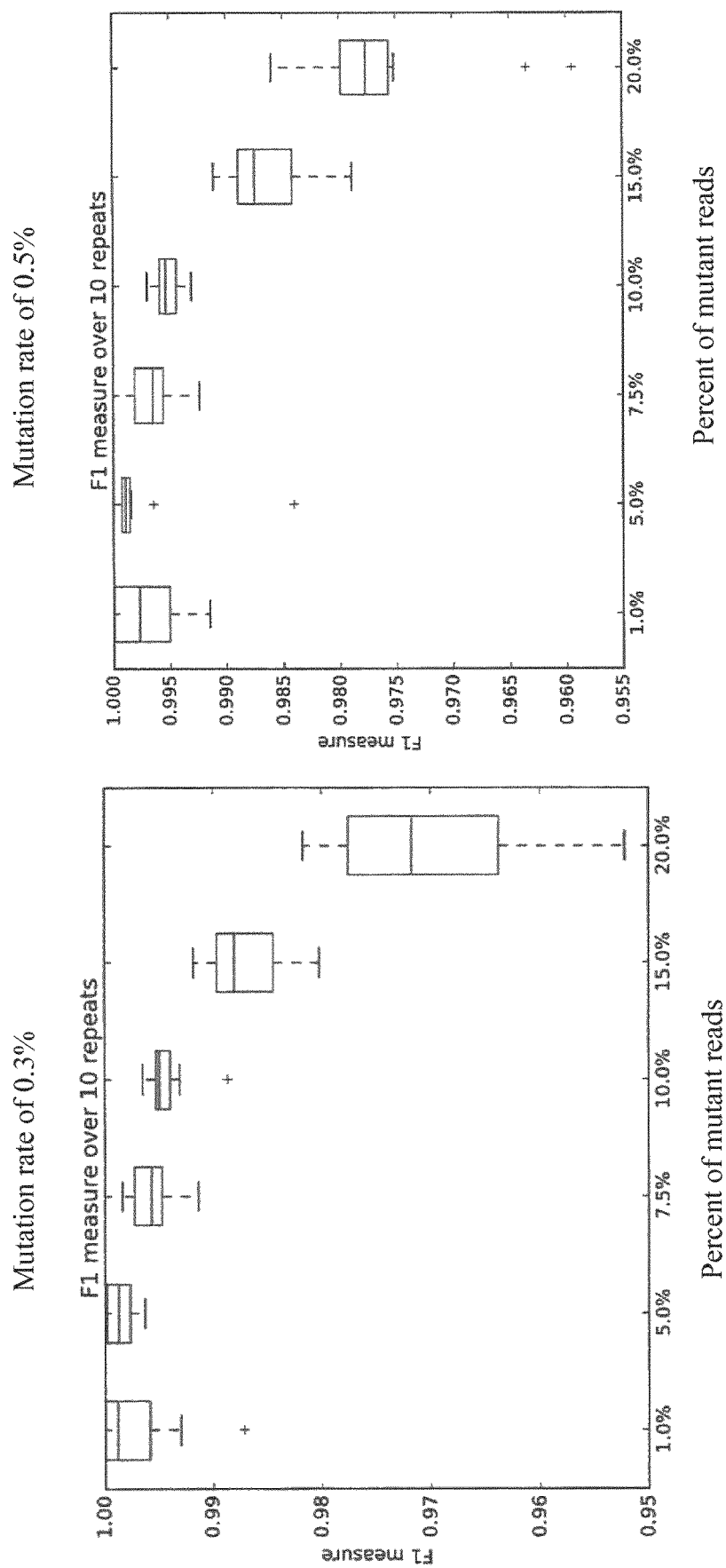
FIG. 9A illustrates example results of identifying subpopulations of HIV-B genomes.
FIG. 9B illustrates example results of identifying subpopulations of HIV-B genomes.

FIGS. 9A and 9B illustrates example results of identifying subpopulations of HIV-B genomes with different mutation rates. In the first experiment in FIG. 9A, two copies of the HIV-B genome are created and substitutions are introduced into one of the copies at random at a 0.3% substitution rate (3 substitutions per 1000 bp) to create a mutant pool. Sequence reads are obtained from the respective genomes at a length of up to 2500 bp. Sequence reads having the wild type at tested loci (e.g., having a reference sequence with no substitution introduced) are obtained, and are selected at random and mixed with sequence reads from the mutant pool, such that sequences reads from the mutant pool account for about 1, 5, 7.5, 10, 15, and 20% of all reads. Classification of the mixed sequence reads are performed to recover the two subpopulations of genomes (i.e., wild type genomes and genomes with mutations). The precision value and the recall value of the ability to correctly recover the two subpopulations in each mixture were measured over 10 repeats, and the F1 measures were calculated and plotted in FIG. 9A. As shown in FIG. 9A, the F1 measures are over 95% for all the tests. Therefore, the classification of the subpopulation has a high accuracy. Thus, the disclosed techniques can recover subpopulations of genomes (including quasispecies) with a high confidence level.

In the second experiment in FIG. 9B, two copies of the HIV-B genome are created and substitutions are introduced into one of the copies at random at a 0.5% substitution rate (5 substitutions per 1000 bp) to create a mutant pool. Sequence reads are obtained from the respective genomes at a length of up to 2500 bp. Sequence reads from wild type are obtained, and are selected at random and mixed with sequence reads from the mutant pool, such that sequence reads from the mutant pool account for about 1, 5, 7.5, 10, 15, and 20% of all reads. Classification of the mixed sequence reads are performed to recover the two subpopulations of genomes (i.e., wild type genomes and genomes with mutations). Precision and recall of the ability to correctly recover the two subpopulations in each mixture are measured over 10 repeats, and the F1 measures are calculated plotted in FIG. 9B. As shown in FIG. 9B, the F1 measures are over 95% for all the tests. Therefore, the disclosed techniques can recover subpopulations of genomes (including quasispecies) with a high confidence level.

VII. Example Quasispecies Identification and Treatment

Techniques disclosed herein may be used to identify subspecies of a virus or bacteria in a biological or environmental sample, and treat the subspecies accordingly with medicines that targets the identified subspecies. For example, the techniques may be used to identify subspecies of HIV virus and the corresponding HIV treatment regimen. Those skilled in the art will understand that the techniques may be used to identify and/or treat subspecies of other types of virus, bacteria, or other biological organisms.

HIV is a type of virus called a retrovirus. A retrovirus is a single-stranded positive-sense RNA virus with a DNA intermediate and, as an obligate parasite, targets a host cell. Once inside the host cell cytoplasm, the virus uses its own reverse transcriptase enzyme to produce DNA from its RNA genome, the reverse of the usual pattern, thus retro (backwards). The new DNA is then incorporated into the host cell genome by an integrase enzyme. The host cell then treats the viral DNA as part of its own genome, translating and transcribing the viral genes along with the cell's own genes, producing the proteins required to assemble new copies of the virus. Once the virus infected the host, the infection may persist indefinitely. HIV treatment involves taking medicines that slow the progression of the virus in a patient's body. The medicines used to treat HIV are called antiretrovirals (ARV). These medicines may often be given in combination with other classes of ARVs. This combination therapy is referred to as antiretroviral therapy (ART).

As HIV virus multiplies in the body, the virus sometimes mutates (changes form) and produces variations of itself Variations of HIV virus that develop while a person is taking HIV medicines may lead to drug-resistant strains of HIV. A person may initially be infected with drug-resistant strains of HIV or develop drug-resistant strains of HIV after starting HIV medicines. With drug resistance, HIV medicines that previously controlled a person's HIV may not be effective against the new, drug-resistant strains of HIV. In other words, the HIV medicines may not prevent the drug-resistant strains of HIV from multiplying. Drug resistance can cause HIV treatment to fail. Drug-resistance testing may thus be performed to identify which, if any, HIV medicines would not be effective against a person's HIV, or which subspecies of HIV is drug-resistant. Drug-resistance testing results may help determine which HIV medicines to include in an HIV treatment regimen.

A therapeutic agent for the treatment of HIV may be incorporated into compositions, which in some embodiments are suitable for pharmaceutical use. Such compositions may comprise non-nucleoside reverse transcriptase inhibitors (NNRTIs), nucleoside reverse transcriptase inhibitors (NRTIs), protease inhibitors (PIs), fusion inhibitors, CCR5 antagonists (CCR5s) (also called entry inhibitors), and integrase strand transfer inhibitors (INSTIs). In general, a person's first HIV regimen includes two NRTIs plus an INSTI, an NNRTI, or a PI boosted with cobicistat or ritonavir. Cobicistat or ritonavir may increase (boost) the effectiveness of the PI. The choice of HIV medicines to include in an HIV regimen may depend on the results of drug-resistance testing.

The compositions used to treat different subspecies of virus, bacteria, or other biological organisms may include the peptide or polypeptide, and an acceptable carrier, for example one that is pharmaceutically acceptable. A "pharmaceutically acceptable carrier" includes any and all solvents, dispersion media, coatings, antibacterial and antifungal agents, isotonic and absorption delaying agents, and the like, compatible with pharmaceutical administration. Examples of such carriers or diluents include, but are not limited to, water, saline, Finger's solutions, dextrose solution, and 5% human serum albumin. Liposomes and nonaqueous vehicles such as fixed oils may also be used. Except when a conventional media or agent is incompatible with an active compound, use of these compositions is contemplated. Supplementary active compounds can also be incorporated into the compositions. A therapeutic agent (and any additional therapeutic agent for the treatment of HIV) can be administered by any suitable means, including parenteral, intrapulmonary, intrathecal and intranasal, and, if desired for local treatment, intralesional administration. Parenteral infusions include, e.g., intramuscular, intravenous, intra-arterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

For example, in some embodiments, subsequent to the step of identifying a subject as having a subspecies of HIV, one or more therapeutic agents (HIV regimen) targeting the subspecies may be administered to the subject. The route of administration of a therapeutic agent can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art. In some embodiments, the therapeutic agent is administered orally, intravenously, or intraperitoneally. In some embodiments, the therapeutic agent is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is within the capability of those skilled in the art.

In some embodiments, a therapeutic agent may be administered to the subject over an extended period of time, e.g., for at least 30, 40, 50, 60, 70, 80, 90, 100, 150, 200, 250, 300, 350 day or longer.

VIII. Example Sequence Analytical System

Figure 10:
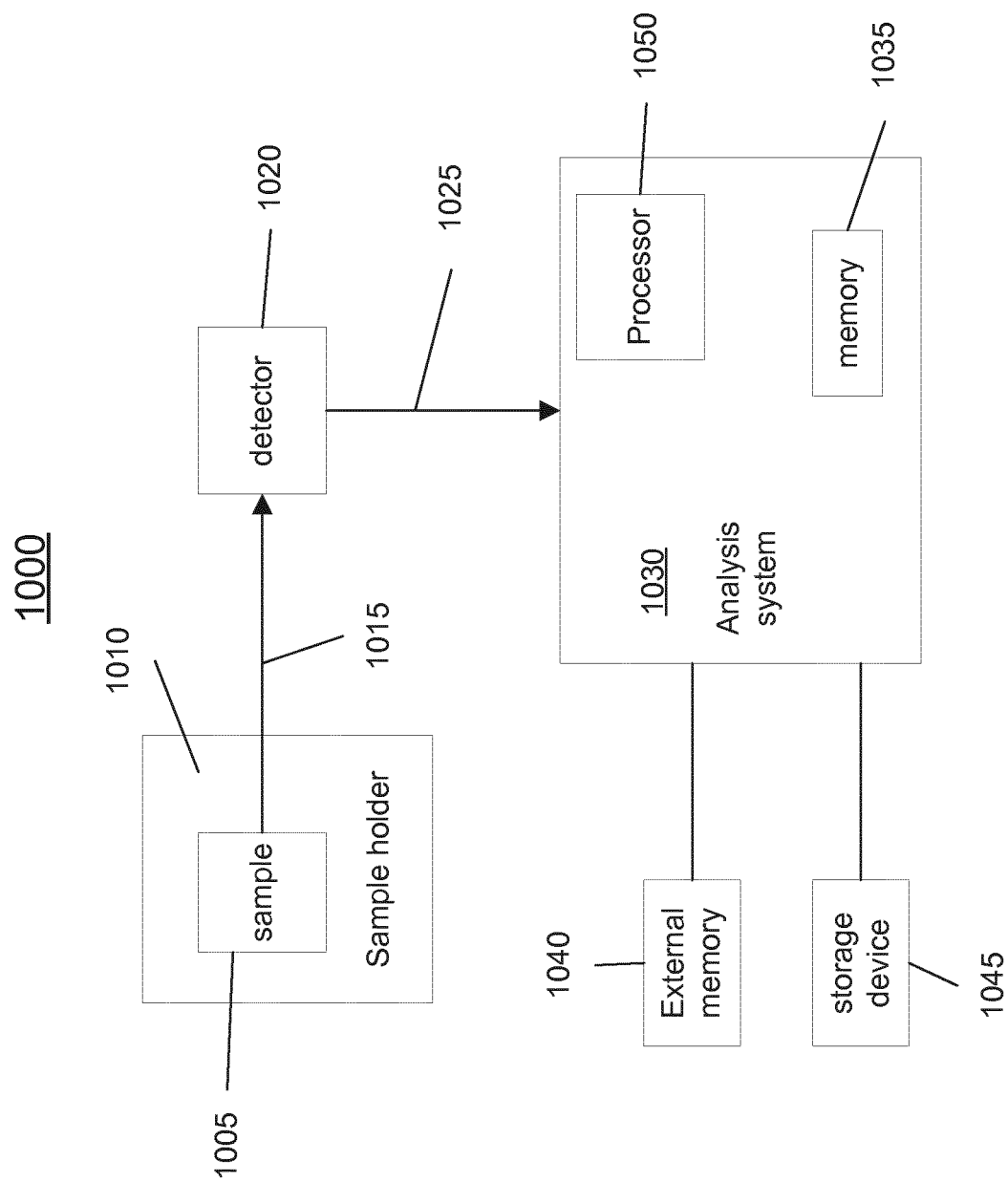
FIG. 10 illustrates a simplified sequence analytical system, according to an aspect of this disclosure.

FIG. 10 illustrates a simplified sequence analytical system 1000 according to an embodiment. System 1000 as shown includes a sample 1005, such as a DNA molecule, within a sample holder 1010, e.g., a chip with an array of spots, wells, or nanopores that contain immobilized DNA. A physical characteristic 1015, such as a fluorescence intensity value, from sample 1005 is detected by a detector 1020. A data signal 1025 from detector 1020 can be sent to analysis system 1030, which may include a processor 1050 and a memory 1035. Data signal 1025 may be stored locally in analysis system 1030 in memory 1035, or externally in an external memory 1040 or a storage device 1045.

Detector 1020 can detect a variety of physical signals, such as light (e.g., fluorescent light from different probes for different bases) or electrical signals (e.g., as created from a molecule traveling through a nanopore).

Analysis system 1030 may be, or may include, a computer system, ASIC, microprocessor, cloud computing system, etc. It may also include or be coupled with a display (e.g., monitor, LED display, etc.) and a user input device (e.g., mouse, keyboard, buttons, etc.). Analysis system 1030 and the other components may be part of a stand-alone or network connected computer system, or they may be directly attached to or incorporated in a device (e.g., a sequencing device) that includes detector 1020 and/or sample holder 1010. Analysis system 1030 may also include software that executes in processor 1050.

IX. Computer System

Figure 11:
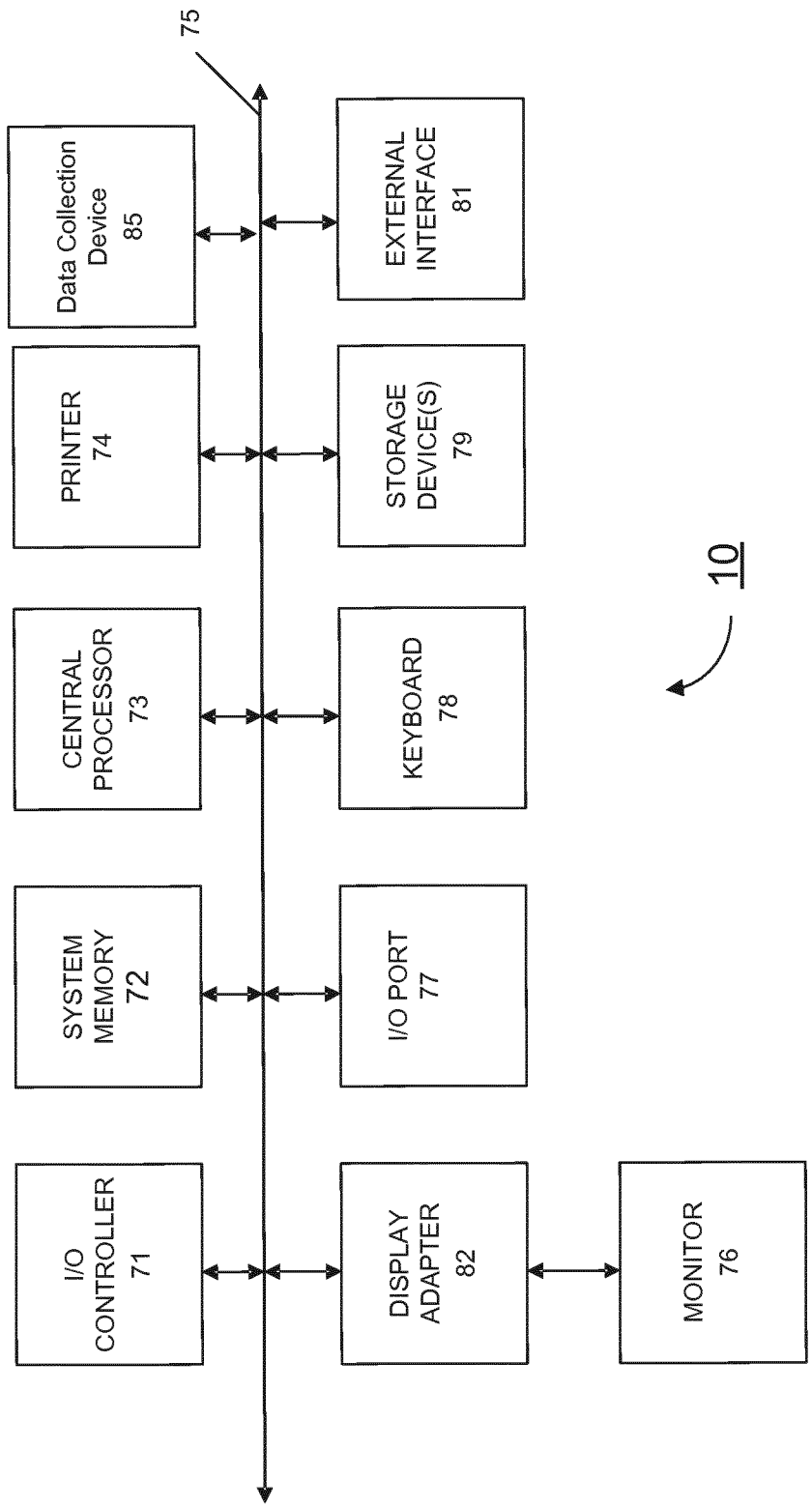
FIG. 11 illustrates an example computer system that may be utilized to implement techniques disclosed herein.

Any of the computer systems mentioned herein may utilize any suitable number of subsystems. Examples of such subsystems are shown in FIG. 11 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 11 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

The invention claimed is:

1. A method comprising:
performing an assay on DNA molecules in one or more samples to obtain a plurality of long sequence reads such that at least some variants in the long sequence reads occur at a frequency above a sequencer noise floor, wherein the one or more samples include a group of organisms of a same species, wherein at least some of the organisms of the same species have different genomes, wherein the plurality of long sequence reads includes at least 100 long sequences reads, and wherein each long sequence read is at least 1000 bases in length;
generating, by a computing system, a variant matrix characterized by a plurality of rows and a plurality of columns, wherein each row of the plurality of rows of the variant matrix represents a long sequence read, wherein each column of the plurality of columns of the variant matrix corresponds to a variant that satisfies one or more quality criteria, wherein the one or more quality criteria comprise: (i) a number of long sequence reads at a locus of the variant is greater than a predetermined threshold, (ii) a frequency of occurrence of the variant at a locus is greater than a predetermined threshold, or (iii) both (i) and (ii), and wherein generating the variant matrix comprises:
determining a total number of the long sequence reads;
comparing the long sequence reads to a reference sequence to identify variant loci;

determining a total number of variant loci that meet the one or more quality criteria;
generating the variant matrix based on the total number of the long sequence reads and the total number of variant loci that satisfy the one or more quality criteria; and
populating column values of the columns of each row of the variant matrix based on a presence or absence of the variants that satisfy the one or more quality criteria in each of the long sequence reads;
creating, by the computing system, a hierarchy of clusters for the plurality of rows of the variant matrix based on differences in the column values among the plurality of rows of the variant matrix;
splitting, by the computing system, the hierarchy of clusters into clusters representing different quasispecies of the genomes; and
identifying one or more quasispecies for a sample in the one or more samples based on the clusters representing the different quasispecies of the genomes.

2. The method of claim 1, wherein splitting the hierarchy of clusters into clusters representing different quasispecies of the genomes comprises:
splitting the hierarchy of clusters into clusters representing different quasispecies of the genomes using an objective function that minimizes a cost at each node.

3. The method of claim 1, wherein the variant matrix has M rows and N columns, wherein M is the total number of the long sequence reads, and N is the total number of variant loci that meet the one or more quality criteria, wherein a variant locus is a locus that a variant occurs, and wherein a column value of a column corresponding to a variant locus of a row corresponding to a long sequence read of the variant matrix is 1 when the variant occurs at the locus of the long sequence read, and a column value of a column corresponding to a variant locus of a row corresponding to a long sequence read of the variant matrix is 0 when the variant does not occur at the locus of the long sequence read.

4. The method of claim 1, further comprising, prior to the creating the hierarchy of clusters, collapsing rows of the variant matrix that are identical.

5. The method of claim 1, wherein the hierarchy of clusters is split to minimize intra-cluster differences.

6. The method of claim 1, wherein the assay is a long amplicon assay.

7. The method of claim 1, wherein splitting the hierarchy of clusters into clusters representing different quasispecies of the genomes comprises:

solving $OPT(u) = \min\{Q(u), OPT(v) + OPT(w)\}$, wherein u is a non-leaf node in the hierarchy; v and w are child nodes of u; Q(u) is a quality value of merging all leaf nodes under node u into a single cluster; OPT(v) is a cost of node v; OPT(w) is a cost of node w; and OPT(u) is a cost of node u.

8. The method of claim 7, wherein the quality value Q(u) comprises an average distance between all reads under node u in the hierarchy.

9. The method of claim 7, wherein splitting the hierarchy of clusters into clusters representing different quasispecies of the genomes further comprises:
determining that Q(u) is greater than a sum of OPT(v) and OPT(w); and
splitting the hierarchy of clusters at node v and node w.

10. The method of claim 7, wherein splitting the hierarchy of clusters into clusters representing different quasispecies of the genomes further comprises:
determining that Q(u) is no greater than a sum of OPT(v) and OPT(w);
setting OPT(u) to Q(u); and
determining a cost of a parent node of non-leaf node u in the hierarchy based on OPT(u).

11. The method of claim 1, further comprising performing a disease diagnosis or providing a treatment plan based on the identified quasispecies for the sample.

12. The method of claim 1, wherein the differences among the plurality of rows of the variant matrix include one or more of a Hamming distance, correlation, cosine correlation, Tanimoto coefficient, Euclidean distance, city block distance, square Euclidean distance, or half square Euclidean distance.

13. The method of claim 11, wherein the providing the treatment plan comprises administering a therapeutically effective amount of a therapeutic agent based on the identified quasispecies for the sample.

14. The method of claim 11, wherein the providing the treatment plan comprises determining one or more therapeutic agents based on the identified quasispecies for the sample and administering a therapeutically effective amount of the one or more therapeutic agent based on the identified quasispecies for the sample.

15. A computer-program product tangibly embodied in a non- transitory machine-readable storage medium, including instructions configured to cause one or more data processors to perform actions including:
performing an assay on DNA molecules in one or more samples to obtain a plurality of long sequence reads such that at least some variants in the long sequence reads occur at a frequency above a sequencer noise floor, wherein the one or more samples include a group of organisms of a same species, wherein at least some of the organisms of the same species have different genomes, and wherein the plurality of long sequence reads includes at least 100 long sequences reads, and wherein each long sequence read is at least 1000 bases in length;
generating a variant matrix characterized by a plurality of rows and a plurality of columns, wherein each row of the plurality of rows of the variant matrix represents a single long sequence read, wherein each column of the plurality of columns of the variant matrix corresponds to a variant that satisfies one or more quality criteria, wherein the one or more quality criteria comprise: (i) a number of long sequence reads at a locus of the variant is greater than a predetermined threshold, (ii) a frequency of occurrence of the variant at a locus is greater than a predetermined threshold, or (iii) both (i) and (ii), and wherein generating the variant matrix comprises:
determining a total number of the long sequence reads;
comparing the long sequence reads to a reference sequence to identify variant loci;
determining a total number of variant loci that meet the one or more quality criteria;
generating the variant matrix based on the total number of the long sequence reads and the total number of variant loci that satisfy the one or more quality criteria; and
populating column values of the columns of each row of the variant matrix based on a presence or absence of the variants that satisfy the one or more quality criteria in each of the long sequence reads;

creating a hierarchy of clusters for the plurality of rows of the variant matrix based on differences in the column values among the plurality of rows of the variant matrix;
splitting the hierarchy of clusters into clusters representing different quasispecies of the genomes; and
identifying one or more quasispecies for a sample in the one or more samples based on the clusters representing the different quasispecies of the genomes.

16. The computer-program product of claim 15, wherein splitting the hierarchy of clusters into clusters representing different quasispecies of the genomes comprises:

solving $OPT(u) = \min\{Q(u), OPT(v) + OPT(w)\}$, wherein u is a non-leaf node in the hierarchy; v and w are child nodes of u; Q(u) is a quality value of merging all leaf nodes under node u into a single cluster; OPT(v) is a cost of node v; OPT(w) is a cost of node w; and OPT(u) is a cost of node u.

17. The computer-program product of claim 16, wherein the quality value Q(u) comprises an average distance between all reads under node u in the hierarchy.

18. A system comprising:
one or more data processors; and
a non-transitory computer readable storage medium containing instructions which, when executed on the one or more data processors, cause the one or more data processors to perform actions including:
performing an assay on DNA molecules in one or more samples to obtain a plurality of long sequence reads such that at least some variants in the long sequence reads occur at a frequency above a sequencer noise floor, wherein the one or more samples include a group of organisms of a same species, wherein at least some of the organisms of the same species have different genomes, and wherein the plurality of long sequence reads includes at least 100 long sequences reads, and wherein each long sequence read is at least 1000 bases in length;
generating, by a computing system, a variant matrix characterized by a plurality of rows and a plurality of columns, wherein each row of the plurality of rows of the variant matrix represents a long sequence read, wherein each column of the plurality of columns of the variant matrix corresponds to a variant that satisfies one or more quality criteria, wherein the one or more quality criteria comprise: (i) a number of long sequence reads at a locus of the variant is greater than a predetermined threshold, (ii) a frequency of occurrence of the variant at a locus is greater than a predetermined threshold, or (iii) both (i) and (ii), and wherein generating the variant matrix comprises:
determining a total number of the long sequence reads;
comparing the long sequence reads to a reference sequence to identify variant loci;
determining a total number of variant loci that meet the one or more quality criteria;
generating the variant matrix based on the total number of the long sequence reads and the total number of variant loci that satisfy the one or more quality criteria; and
populating column values of the columns of each row of the variant matrix based on a presence or absence of the variants that satisfy the one or more quality criteria in each of the long sequence reads;
creating, by the computing system, a hierarchy of clusters for the plurality of rows of the variant matrix based on differences in the column values among the plurality of rows of the variant matrix;
splitting, by the computing system, the hierarchy of clusters into clusters representing different quasispecies of the genomes; and
identifying one or more quasispecies for a sample in the one or more samples based on the clusters representing the different quasispecies of the genomes.

19. The system of claim 18, wherein splitting the hierarchy of clusters into clusters representing different quasispecies of the genomes comprises:

solving $OPT(u) = \min\{Q(u), OPT(v) + OPT(w)\}$, wherein u is a non-leaf node in the hierarchy; v and w are child nodes of u; Q(u) is a quality value of merging all leaf nodes under node u into a single cluster; OPT(v) is a cost of node v; OPT(w) is a cost of node w; and OPT(u) is a cost of node u.

* * * * *